United States Patent [19]

Vanderspurt et al.

[11] Patent Number: 5,504,262
[45] Date of Patent: Apr. 2, 1996

[54] DIRECT CATALYTIC CONVERSION OF METHANE TO ETHANOL

[75] Inventors: Thomas H. Vanderspurt, Hunterdon County; John J. Knarr, Flemington; Anthony W. Ho, Annandale, all of N.J.

[73] Assignee: Exxon Research & Engineering Co., Florham Park, N.J.

[21] Appl. No.: 363,473

[22] Filed: Dec. 23, 1994

[51] Int. Cl.⁶ .......................... C07B 41/02; C07B 41/00
[52] U.S. Cl. ........................................ 568/910.5; 568/950
[58] Field of Search .................... 568/910.5, 910

[56] References Cited

U.S. PATENT DOCUMENTS

| | | | |
|---|---|---|---|
| 891,753 | 6/1908 | Von Unruh et al. | 568/910 |
| 1,858,822 | 5/1932 | Frolich | 568/910.5 |
| 3,092,667 | 6/1963 | Murphy | 568/910 |
| 4,045,498 | 8/1977 | Deno | 568/910 |
| 4,900,871 | 2/1990 | Ellis, Jr. | 568/910 |
| 4,982,023 | 1/1991 | Han et al. | 568/910 |
| 5,012,029 | 4/1991 | Han et al. | 568/910 |
| 5,017,732 | 5/1991 | Gesser et al. | 568/910 |
| 5,132,472 | 7/1992 | Durante et al. | 568/910.5 |
| 5,347,057 | 9/1994 | Khan | 568/910 |

FOREIGN PATENT DOCUMENTS

| | | |
|---|---|---|
| 296712 | 12/1988 | European Pat. Off. . |
| 3101024 | 1/1981 | Germany . |
| 256239 | 9/1994 | Japan . |
| 7297 | 3/1905 | United Kingdom . |
| 2157688 | 10/1985 | United Kingdom . |
| 90/0516 | 5/1990 | WIPO . |

OTHER PUBLICATIONS

Koerts, et al. JACS, 114, 7272–7278 (1992).
Lin, et al. JACS, 114, 7307–7308 (1992).
Lin, et al. JACS, 114, No. 18 7279 (Nov. 18, 1992).
Neumann, et al. J.A.C.S. (1992) 114, 7278–7286.
Stenberg, et al. Symp. On Jet Fuels III A.C.S., Div. of Petroleum Chem., A.C.S. San Francisco Meeting, Apr. 5–10 (1992) pp. 576–579.

Primary Examiner—Paul J. Killos
Attorney, Agent, or Firm—Linda M. Scuorzo

[57] ABSTRACT

The present invention relates to a method for making mixtures of ethanol and methanol by reacting methane, water and an acidic aqueous solution of a electron acceptor, preferably $Fe_2(SO_4)_3$ or $Fe(ClO_4)_3$, having a pH of less than 3, preferably 1 to 3, more preferably 1 to 2 in the presence of a noble metal catalyst, typically platinum or palladium, having a diameter of at least about 100 Å at a temperature of at least 60° C. to about 100° C. The process is advantageous as it provides a method of making ethanol directly from methanol at low cost and high thermodynamic efficiency.

6 Claims, No Drawings

DIRECT CATALYTIC CONVERSION OF METHANE TO ETHANOL

FIELD OF THE INVENTION

The present invention relates to a process for catalytically converting methane to primarily ethanol.

Currently, methanol is almost exclusively synthesized from gases containing CO and $H_2$. An alternative process for catalytically producing methanol from methane is disclosed in German patent DE3101021A1 to Koenig, in which methanol with a minor amount of $CO_2$ is formed from methane using an acidic solution of iron (III) sulfate having a pH value of less than 3, preferably less than about 1 as the oxygen supplier in the presence of a catalyst of platinum or palladium on a carbon carrier at a reaction temperature of 10°–50° C. and 30–60 bar. The $Fe^{+3}$ subsequently may be separately re-oxidized and re-used. However, no ethanol is produced.

It would be desirable to directly convert methane to a mixture of ethanol and methanol using similar technologies as they offer the advantage of high thermodynamic efficiency and potentially low capital cost. Applicants' process presents such advantages.

SUMMARY OF THE INVENTION

The present invention provides for a method for producing a mixture of methanol and ethanol by contacting methane, water and an acidic aqueous solution of an electron acceptor selected from the group consisting of $Fe_2(SO_4)_3$ and $Fe(Cl_4)_3$ having a pH of less than 3 with a noble metal catalyst selected from the group consisting of platinum and palladium at a temperature of at least about 60° C. to form a mixture containing primarily methanol and ethanol.

The present invention may suitably comprise, consist or consist essentially of the elements or steps disclosed herein and may be practiced in the absence of an element or step not disclosed.

DETAILED DESCRIPTION OF THE INVENTION

Applicant's process provides a one step method for directly and preferentially making ethanol, typically in a mixture containing ethanol and methanol, from methane by reacting methane, water and an electron acceptor in the presence of a noble or metal containing alloy catalyst of Group VIII of the Periodic Table, preferably Pt and Pd, more preferably platinum. Platinum black is an example of a preferred form of a noble metal catalyst. Other elements from Group VIII or Group IB may be present but these should not limit methyl group migration across the surface of the metal nor encourage the stripping of more than one hydrogen of chemsorbed methane. This last requirement tends to exclude Rh and Ir. The catalyst should not react with the electron acceptor solution, thus significant concentrations of metals such as Fe, Co, Ni and Cu tend to be excluded. The catalyst can be up to essentially 100% metal as in a Pt black or more dilute metal to at least about 5 wt %. The noble metal crystallites are required to be greater than 100 Å. The noble metal catalyst may be supported on an inorganic oxide that is insoluble in acidic media or on a low surface area carbonacious or other insoluble support.

The reaction may be carried out for example, in a trickle bed or a slurry reactor to minimize mass transfer limitations and provide good contacting between the methane containing gas and the solution and between the solution and the catalyst surface.

The reaction pressures can be from at least 30 atm to as high as practical, for example 200 atm. However, in order to produce ethanol as well as methanol in the product mixture reaction temperatures are from about 60° C. to about 100° C. preferably from 70° C. to 90° C.

The process of the present invention produces mixtures containing methanol and ethanol. Other oxygenates such as propanol, acetaldehyde, acetic acid and the like as well as $CO_2$ may be present depending on the combination of residence time, temperature, methane pressure and the like.

It is preferred that the reaction be carried out in the absence of compounds that are catalyst poisons, such as, compounds of S, Se and the like. It is also preferred that the reaction be carried out in the absence of carbon monoxide, olefins, HCN or other cyanide containing substances. It is optional, but very desirable to remove the resulting oxygenates as they are formed in order to minimize their further oxidation, ultimately to $CO_2$. This may be accomplished by means known in the art.

The electron acceptor is preferably a transition metal complex, or may be an electrical circuit wherein the metal containing catalyst is part of a suitably constructed electrode.

When the electron acceptor is a transition metal complex it is an acidic aqueous solution of a salt of the transition metal. The transition metal should be one that can function as an electron acceptor (oxidizing agent) in an aqueous solution, preferably $Fe^{+3}$. It should also be capable of being re-oxidized after reduction and be soluble in the reactant solution in its reduced state under the conditions of reoxidation. This may be accomplished by adjusting the pH by adding dilute acid or other appropriate means known to those in the art. For example, if iron is used, a dilute acidic aqueous solution of $Fe_2(SO_4)_3$ or $Fe(Cl_4)_3$ is suitable for these purposes, and desirably the acidic aqueous iron formed will have at least 2 water molecules as ligands. However, the pH of the solution should be maintained at a level sufficient to discourage the formation of colloidal gels of the hydrolyzed metal salt, e.g. when the transition metal is iron dilute $Fe^{+3}$ at pH of less than about 3, preferably about 1 to 3, more preferably about 1 to 2 is necessary.

Reoxidation of the reduced electron acceptor complex may be carried out by known methods. For example, an oxygen containing gas such as air may be used. The reoxidation temperature and pressure are determined by the nature of the electron acceptor complex. A typical combination of conditions, for example, could include a pressure of about 3 atm of air at about 130° C. or about 10 atm at about 180° C. If a simple iron aquo complex is used the tendency of $Fe^{+3}(H_2O)_6$ to hydroylyze and the form of insoluble hydrous iron oxide precipitates increases with temperature so the temperature, pH and transition metal concentration should be adjusted accordingly. Optionally this reoxidation may be carried out in the presence of a material such as activated carbon or a noble metal catalyst. Prior to reoxidation it is desirable to remove the product by such means as are known in the art such as distillation or low pressure inert gas stripping.

While Applicants do not wish to be bound by a proposed mechanism it is hypothesized that higher temperatures used and the combination of the larger noble metal crystallites and a more dilute $Fe^{+3}$ solution allows chemisorbed methyl groups formed on the surface by the dissociated chemisorption of methane to react with each other in a form of oxidative coupling yielding ethanol which desorbs from the surface. The site for this coupling being in the vicinity of a chemisorbed aquo-ferric species which provides oxygen for the ethanol product as it withdraws an electron from the chemisorbed species via the Pt surface. Thus the ferric species is reduced to ferrous. Other couples that are stable and soluble in acidic solution such as those involving heteropolymolybdate ions and the like may be used. Couples where in the electron acceptor species is likely to react directly with the product alcohol such as dichromate are excluded. Similarly, couples such as the dichromate-chromic couple that cannot be readily reoxidized by air at moderate pressure (less than 20 atm) and moderate temperatures (less than 200° C.) are excluded, as are couples that tend to give rise to insoluble precipitates or species that poison the catalytic surface. While not wishing to be bound by a theory of operation Applicants believe that methane chemisorbing noble metal with sufficient electron affinity dissociates into a methyl group and a hydrogen species. In the presence of a dilute solution of electron acceptor complexes such as $Fe^{+3}(H_2O)_6$ the hydrogen species is removed as a proton and one electron is taken up by an electron acceptor complex, for example $Fe^{+3}(H_2O)_6$ is converted to $Fe^{+2}(H_2O)_6$. If the noble metal crystallite is sufficiently large, greater than about 100 Å, preferably greater than about 200 Å the chemisorbed methyl group may encounter a second methyl group. If the temperature is sufficiently high, preferably from 60° C. to about 100° C. more preferably from about 70° C. to about 90° C. the methyl groups may migrate and encounter each other with enough energy to react with each other to form a chemisorbed ethyl species and a chemisorbed hydrogen species. The hydrogen is removed by reaction with an electron acceptor complex. The chemisorbed ethyl species undergoes hydrolysis of the noble metal-carbon bond and an ethanol molecule is liberated.

If the temperature is low, as in German Patent DE 3101021A1 to Koenig, or the concentration of the electron acceptor is too high, or the noble metal domain size is too small hydrolysis of the methyl group carbon-platinum bond occurs before another methyl group is encountered with sufficient energy for coupling and methanol is produced. If the temperature is too high the methyl group will react to form a methanol-like species. It is believed that methanol can dissociatively react with the noble metal catalyst surface to give a HO—$CH_2$ noble metal speices and a proton and 2 electrons. This species continues to react by stepwise loss of hydrogen species and electrons until ultimately carbon dioxide is produced. Further, when ethanol is produced ethanol oxidation products are likely since ethanol will react with transition metal ions in the presence of platinum black to yield acetaldehyde and acetic acid. This, as well as the direct oxidation of the nascent methyl groups, in practice sets an upper limit on the reaction temperature of about 100° C., under methane pressures of less than about 70 atmospheres. Thus, Applicants hypothesize that the electron acceptor complex to be effective must interact with the noble metal surface, and although we do not wish to be bound by this, it may in fact participate in the hydrolysis step which converts a noble metal-$CH_2CH_3$ species to ethanol.

In the process of the present invention methane suitably may be obtained from any source. It may be used in pure or essentially pure form, or as a component of a methane containing gas. As the amount (e.g., pressure) of higher ($C_{2+}$) alkanes increases relative to methane, production of ethanol from methane will typically decrease as a proportion of total alcohol produced due to the relatively greater rate of reaction of higher alkane species in these competing reactions. However, by way of example use of ultra high purity methane having less than about 10 ppm $CO_2$ and less than about 10 ppm ethane at the reaction conditions of the present invention was used to minimize the possibility that the ethane present contributed to the production of ethanol from methane. This does not, however, preclude the use of methane containing gas in lieu of pure methane.

It is important to maintain a sufficient supply of methane to the catalyst as the catalyst is typically in contact with a layer of aqueous ionic solution. Typically, this is accomplished by maintaining as high a partial pressure of methane over the solution as possible.

EXAMPLES

Example 1

Preparation of $Fe_2(SO_4)_3$ 25.97701 g $Fe_2(SO_4)_3 \times H_2O$ containing 7.4% water (Johnson-Mathey Puratronic Grade, Lot #K021), and 1.606 grams of Norit activated carbon was placed in a scrupulously clean flask equipped with a scrupulously clean reflux condenser along with about 300 mls of triple distilled water the pH of which had been adjusted to 2.0 with reagent grade $H_2SO_4$. After refluxing until the ferric sulfate was dissolved the solution was cooled and filtered and stored in a tightly closed flask.

Example 2

About 3 grams of the solution from Example 1 was placed in each of eight small, scrupulously clean, Pyrex glass test tubes. All tubes contained about 3 g of solution of $Fe_2(SO_3)_4$ (about 0.4M $Fe^{+3}$ solution, about 1.2 millimoles of $Fe^{+3}$). Platinum black was Aldrich #20-591-5, CAS Reg No [7440-06-4], lot #01021TV CW). The tubes were sealed into a stainless steel pressure vessel and repeatedly pressurized and depressurized with ultra high purity methane which by GC analysis contained an essential absence of ethane and $CO_2$, that is, less than 10 ppm $CO_2$ and less than 10 ppm ethane. The reaction in tubes 1–4 was carried out at about 75° C. and in tubes 5–8 at less than about 50° C. The tubes were examined after reaction for the presence or absence of methanol and ethanol. The results are summarized in Table 1 below. The reaction in Tube 3 produced $0.2 \times 10^{-4}$M methanol and $1.0 \times 10^{-4}$M ethanol. It is believed that Tube 2 contained insufficient Pt black to catalyze the reaction. The temperature for Tubes 5–8 was believed to be lower than that required for the reaction to produce ethanol.

TABLE 1

| Tube No. | g. Pt Black | Methanol Present | Ethanol Present |
|---|---|---|---|
| 1 | 0.0 | No | No |
| 2 | 0.0088 | No | No |
| 3 | 0.0246 | Yes | Yes |
| 4 | 0.0287 | Yes | Yes |
| 5 | 0.0409 | No | No |
| 6 | 0.0585 | No | No |
| 7 | 0.0754 | No | No |
| 8 | 0.1084 | No | No |

What is claimed is:

1. A method for producing a mixture of methanol and ethanol, comprising: contacting methane, water and an acidic aqueous solution of an electron acceptor selected from the group consisting of $Fe_2(SO_4)_3$ and $Fe(ClO_4)_3$ having a pH of less than 3 with a noble metal catalyst selected from the group consisting of platinum and palladium having a particle diameter of at least about 100 Å at a temperature of at least about 60° C. form a mixture containing primarily methanol and ethanol.

2. The method of claim 1 wherein the pH is from 1 to about 3 and.

3. The method of claim 1 wherein the pH is from 1 to about 2.

4. The process of claim 1 wherein the catalyst is platinum black.

5. The method of claim 1 wherein the temperature is up to 100° C.

6. The process of claim 1 wherein this methane containing gas is essentially free of catalyst poisons.

* * * * *